(12) United States Patent
Nagy et al.

(10) Patent No.: US 9,489,831 B2
(45) Date of Patent: Nov. 8, 2016

(54) WIRELESS SENSOR READER

(71) Applicant: Endotronix, Inc., East Peoria, IL (US)

(72) Inventors: Michael Nagy, Lawrenceville, GA (US); Harry D. Rowland, Plainfield, IL (US); Roger Dwight Watkins, Dunlap, IL (US); Balamurugan Sundaram, Dunlap, IL (US)

(73) Assignee: Endotronix, Inc., East Peoria, IL (US)

( * ) Notice: Subject to any disclaimer, the term of this patent is extended or adjusted under 35 U.S.C. 154(b) by 237 days.

(21) Appl. No.: 14/041,738

(22) Filed: Sep. 30, 2013

(65) Prior Publication Data
US 2014/0028467 A1 Jan. 30, 2014

Related U.S. Application Data

(63) Continuation of application No. 13/455,776, filed on Apr. 25, 2012, now Pat. No. 8,570,186, which is a continuation-in-part of application No. 13/423,693, filed on Mar. 19, 2012, now Pat. No. 8,432,265, which (Continued)

(51) Int. Cl.
*H04Q 5/22* (2006.01)
*G05B 11/00* (2006.01)
(Continued)

(52) U.S. Cl.
CPC .............. *G08C 17/02* (2013.01); *A61B 5/0031* (2013.01); *A61B 5/0215* (2013.01); *A61B 5/6882* (2013.01); *A61B 5/7225* (2013.01)

(58) Field of Classification Search
CPC .......... A61B 5/0031; A61B 2562/028; A61B 5/0215; A61B 2560/0219; A61B 2560/0257; A61B 2560/0242; A61B 5/026; A61B 5/031; A61B 5/076; A61B 5/145
See application file for complete search history.

(56) References Cited

U.S. PATENT DOCUMENTS 3,714,595 A * 1/1973 Denenberg et al. .......... 329/356
3,872,455 A 3/1975 Fuller et al.
(Continued)

FOREIGN PATENT DOCUMENTS

| WO | WO2005/107583 | 11/2005 |
| WO | WO2006/130488 | 12/2006 |
| WO | WO2012/149008 | 11/2012 |

OTHER PUBLICATIONS

The International Bureau of WIPO, International Search Report and Written Opinion of International Searching Authority, Endotronix, Inc., PCT Application No. PCT/US2010/27951, Aug. 25, 2010.
The International Bureau of WIPO, International Search Report and Written Opinion of International Searching Authority, Nunez, Anthony I., PCT Application No. PCT/US2008/03475, Aug. 4, 2008.
Haynes, H.E. & Witchey, A.L., Medical Electronics: The Pill That "Talks", DEP, pp. 52-54, Camden, N.J.
(Continued)

*Primary Examiner* — Steven Lim
*Assistant Examiner* — Muhammad Adnan
(74) *Attorney, Agent, or Firm* — McDonald Hopkins LLC

(57) ABSTRACT

A wireless sensor reader is provided to interface with a wireless sensor. The wireless sensor reader transmits an excitation pulse to cause the wireless sensor to generate a ring signal. The wireless sensor reader receives and amplifies the ring signal and sends the signal to a phase-locked loop. A voltage-controlled oscillator in the phase-locked loop locks onto the ring signal frequency and generates a count signal at a frequency related to the ring signal frequency. The voltage-controlled oscillator is placed into a hold mode where the control voltage is maintained constant to allow the count signal frequency to be determined. The reader uses an ambient reading or other information to select a subset of the possible ring signal frequencies, and tunes or adjusts its circuits and algorithms to focus on that subset.

41 Claims, 3 Drawing Sheets

Related U.S. Application Data is a continuation of application No. 12/419,326, filed on Apr. 7, 2009, now Pat. No. 8,154,389, which is a continuation-in-part of application No. 12/075,858, filed on Mar. 14, 2008, now abandoned.

(60) Provisional application No. 61/478,647, filed on Apr. 25, 2011, provisional application No. 60/918,164, filed on Mar. 15, 2007.

(51) Int. Cl.
| | |
|---|---|
| G08C 19/16 | (2006.01) |
| G08B 29/00 | (2006.01) |
| G08B 1/00 | (2006.01) |
| G08B 1/08 | (2006.01) |
| G08B 21/00 | (2006.01) |
| G08B 13/20 | (2006.01) |
| G08C 17/02 | (2006.01) |
| A61B 5/00 | (2006.01) |
| A61B 5/0215 | (2006.01) |

(56) References Cited

U.S. PATENT DOCUMENTS

| | | | |
|---|---|---|---|
| 3,888,708 | A | 6/1975 | Wise et al. |
| 3,943,915 | A | 3/1976 | Severson |
| 4,023,562 | A | 5/1977 | Hynecek et al. |
| 4,026,276 | A | 5/1977 | Chubbuck |
| 4,067,235 | A | 1/1978 | Markland et al. |
| 4,127,110 | A | 11/1978 | Bullara |
| 4,206,762 | A | 6/1980 | Cosman |
| 4,385,636 | A | 5/1983 | Cosman |
| 4,407,296 | A | 10/1983 | Anderson |
| 4,481,514 | A * | 11/1984 | Beukers .............. G01W 1/08 340/870.1 |
| 4,485,813 | A | 12/1984 | Anderson et al. |
| 4,511,858 | A | 4/1985 | Charavit et al. |
| 4,531,526 | A | 7/1985 | Genest |
| 4,567,459 | A | 1/1986 | Folger et al. |
| 4,644,420 | A | 2/1987 | Buchan |
| 4,651,089 | A | 3/1987 | Haigh |
| 4,815,472 | A | 3/1989 | Wise et al. |
| 4,881,410 | A | 11/1989 | Wise et al. |
| 4,953,387 | A | 9/1990 | Johnson et al. |
| 5,005,577 | A | 4/1991 | Frenkel |
| 5,006,819 | A | 4/1991 | Buchan et al. |
| 5,013,396 | A | 5/1991 | Wise et al. |
| 5,046,497 | A | 9/1991 | Millar |
| 5,055,838 | A | 10/1991 | Wise et al. |
| 5,059,543 | A | 10/1991 | Wise et al. |
| 5,108,420 | A | 4/1992 | Marks |
| 5,113,868 | A | 5/1992 | Wise et al. |
| 5,257,630 | A | 11/1993 | Broitman et al. |
| 5,262,127 | A | 11/1993 | Wise et al. |
| 5,282,827 | A | 2/1994 | Kensey et al. |
| 5,296,255 | A | 3/1994 | Gland et al. |
| 5,334,952 | A | 8/1994 | Maddy et al. |
| 5,343,064 | A | 8/1994 | Spangler et al. |
| 5,377,524 | A | 1/1995 | Wise et al. |
| 5,417,235 | A | 5/1995 | Wise et al. |
| 5,564,434 | A | 10/1996 | Halperin et al. |
| 5,581,248 | A | 12/1996 | Spillman, Jr. et al. |
| 5,690,674 | A | 11/1997 | Diaz |
| 5,872,520 | A * | 2/1999 | Seifert et al. ............. 340/5.61 |
| 5,920,233 | A | 7/1999 | Denny |
| 5,992,769 | A | 11/1999 | Wise et al. |
| 6,015,386 | A | 1/2000 | Kensey et al. |
| 6,025,725 | A | 2/2000 | Gershenfeld et al. |
| 6,109,113 | A | 8/2000 | Chavan et al. |
| 6,111,520 | A | 8/2000 | Allen et al. |
| 6,113,553 | A * | 9/2000 | Chubbuck ............. A61B 5/0031 600/561 |
| 6,126,675 | A | 10/2000 | Shchervinsky et al. |
| 6,140,144 | A | 10/2000 | Najafi et al. |
| 6,174,322 | B1 | 1/2001 | Schneidt |
| 6,190,400 | B1 | 2/2001 | Van De Moer et al. |
| 6,206,835 | B1 | 3/2001 | Spillman, Jr. et al. |
| 6,232,150 | B1 | 5/2001 | Lin et al. |
| 6,278,379 | B1 | 8/2001 | Allen et al. |
| 6,287,256 | B1 | 9/2001 | Park et al. |
| 6,309,350 | B1 | 10/2001 | VanTassel et al. |
| 6,331,163 | B1 | 12/2001 | Kaplan |
| 6,338,284 | B1 | 1/2002 | Najafi et al. |
| 6,359,444 | B1 * | 3/2002 | Grimes .............. 324/633 |
| 6,447,449 | B1 | 9/2002 | Fleischman et al. |
| 6,454,720 | B1 | 9/2002 | Clerc et al. |
| 6,471,656 | B1 | 10/2002 | Shalman et al. |
| 6,477,901 | B1 | 11/2002 | Tadigadapa et al. |
| 6,499,354 | B1 | 12/2002 | Najafi et al. |
| 6,570,457 | B2 | 5/2003 | Fischer |
| 6,592,608 | B2 | 7/2003 | Fisher et al. |
| 6,636,769 | B2 | 10/2003 | Govari et al. |
| 6,645,143 | B2 | 11/2003 | VanTassel et al. |
| 6,647,778 | B2 | 11/2003 | Sparks |
| 6,658,300 | B2 | 12/2003 | Govari et al. |
| 6,666,826 | B2 | 12/2003 | Salo et al. |
| 6,667,725 | B1 | 12/2003 | Simons et al. |
| 6,680,654 | B2 | 1/2004 | Fischer et al. |
| 6,682,490 | B2 | 1/2004 | Roy et al. |
| 6,713,828 | B1 | 3/2004 | Chavan et al. |
| 6,749,622 | B2 | 6/2004 | McGuckin, Jr. et al. |
| 6,764,446 | B2 | 7/2004 | Wolinsky et al. |
| 6,779,406 | B1 | 8/2004 | Kuznia et al. |
| 6,783,499 | B2 | 8/2004 | Schwartz |
| 6,824,521 | B2 | 11/2004 | Rich et al. |
| 6,838,640 | B2 | 1/2005 | Wise et al. |
| 6,844,213 | B2 | 1/2005 | Sparks |
| 6,855,115 | B2 | 2/2005 | Fonseca et al. |
| 6,890,300 | B2 | 5/2005 | Lloyd et al. |
| 6,893,885 | B2 | 5/2005 | Lemmerhirt et al. |
| 6,916,310 | B2 | 7/2005 | Sommerich |
| 6,923,625 | B2 | 8/2005 | Sparks |
| 6,926,670 | B2 | 8/2005 | Rich et al. |
| 6,932,114 | B2 | 8/2005 | Sparks |
| 6,935,010 | B2 | 8/2005 | Tadigadpa et al. |
| 6,939,299 | B1 | 9/2005 | Petersen et al. |
| 6,959,608 | B2 | 11/2005 | Bly et al. |
| 6,968,743 | B2 | 11/2005 | Rich et al. |
| 6,981,958 | B1 | 1/2006 | Gharib et al. |
| 7,001,398 | B2 | 2/2006 | Carley et al. |
| 7,004,015 | B2 | 2/2006 | Chang-Chien et al. |
| 7,013,734 | B2 | 3/2006 | Zdeblick et al. |
| 7,028,550 | B2 | 4/2006 | Zdeblick et al. |
| 7,046,964 | B1 | 5/2006 | Sullivan et al. |
| 7,048,756 | B2 | 5/2006 | Eggers et al. |
| 7,059,176 | B2 | 6/2006 | Sparks |
| 7,059,195 | B1 | 6/2006 | Liu et al. |
| 7,066,031 | B2 | 6/2006 | Zdeblick et al. |
| 7,073,387 | B2 | 7/2006 | Zdeblick et al. |
| 7,081,125 | B2 | 7/2006 | Edwards et al. |
| 7,137,953 | B2 | 11/2006 | Eigler et al. |
| 7,146,861 | B1 | 12/2006 | Cook et al. |
| 7,147,604 | B1 | 12/2006 | Allen et al. |
| 7,149,587 | B2 | 12/2006 | Wardle et al. |
| 7,162,926 | B1 | 1/2007 | Guziak et al. |
| 7,190,937 | B1 | 3/2007 | Sullivan et al. |
| 7,192,001 | B2 | 3/2007 | Wise et al. |
| 7,198,603 | B2 | 4/2007 | Penner et al. |
| 7,211,048 | B1 * | 5/2007 | Najafi .............. A61B 5/0031 600/481 |
| 7,228,735 | B2 | 6/2007 | Sparks et al. |
| 7,245,117 | B1 | 7/2007 | Joy et al. |
| 7,273,457 | B2 | 9/2007 | Penner |
| 7,284,442 | B2 | 10/2007 | Fleischman et al. |
| 7,290,454 | B2 | 11/2007 | Liu |
| 7,425,200 | B2 | 9/2008 | Brockway et al. |
| 7,432,723 | B2 | 10/2008 | Ellis et al. |
| 7,466,120 | B2 | 12/2008 | Miller et al. |
| 7,483,805 | B2 | 1/2009 | Sparks et al. |
| 7,498,799 | B2 | 3/2009 | Allen et al. |
| 7,550,978 | B2 | 6/2009 | Joy et al. |
| 7,566,308 | B2 | 7/2009 | Stahmann |

(56) References Cited

U.S. PATENT DOCUMENTS

| | | | |
|---|---|---|---|
| 7,621,036 B2* | 11/2009 | Cros | A61B 5/0215 205/122 |
| 7,641,619 B2 | 1/2010 | Penner | |
| 7,679,355 B2 | 3/2010 | Allen et al. | |
| 7,813,808 B1* | 10/2010 | Doron | A61B 5/0215 607/59 |
| 7,839,153 B2 | 11/2010 | Joy et al. | |
| 7,909,770 B2* | 3/2011 | Stern | A61B 5/0031 600/485 |
| 7,936,174 B2 | 5/2011 | Ellis et al. | |
| 7,983,745 B2* | 7/2011 | Hatlestad | A61B 5/0031 600/513 |
| 8,154,389 B2 | 4/2012 | Rowland et al. | |
| 8,360,984 B2* | 1/2013 | Yadav | A61B 5/0031 600/486 |
| 8,432,265 B2 | 4/2013 | Rowland et al. | |
| 8,493,187 B2 | 7/2013 | Rowland et al. | |
| 8,558,705 B2* | 10/2013 | Gong | G01N 22/02 29/595 |
| 8,570,186 B2 | 10/2013 | Nagy et al. | |
| 9,332,913 B2* | 5/2016 | Dalal | A61B 5/7239 |
| 2002/0045921 A1 | 4/2002 | Wolinsky et al. | |
| 2002/0072656 A1 | 6/2002 | Vantassel et al. | |
| 2002/0115920 A1 | 8/2002 | Rich et al. | |
| 2002/0138009 A1 | 9/2002 | Brockway et al. | |
| 2002/0151770 A1* | 10/2002 | Noll, III | A61B 5/0031 600/300 |
| 2002/0151816 A1 | 10/2002 | Rich et al. | |
| 2002/0177782 A1* | 11/2002 | Penner | A61B 5/00 600/485 |
| 2002/0188207 A1 | 12/2002 | Richter | |
| 2003/0062957 A1 | 4/2003 | Terashima et al. | |
| 2003/0114898 A1* | 6/2003 | Von Arx | A61N 1/08 607/60 |
| 2003/0136417 A1 | 7/2003 | Fonseca et al. | |
| 2003/0139677 A1 | 7/2003 | Fonseca et al. | |
| 2003/0139771 A1 | 7/2003 | Fisher et al. | |
| 2003/0158584 A1 | 8/2003 | Cates et al. | |
| 2003/0191496 A1 | 10/2003 | Edwards et al. | |
| 2004/0102806 A1 | 5/2004 | Broome et al. | |
| 2004/0158138 A1 | 8/2004 | Kilcoyne et al. | |
| 2004/0172083 A1* | 9/2004 | Penner | A61B 5/0031 607/35 |
| 2004/0220637 A1 | 11/2004 | Zdeblick et al. | |
| 2004/0255643 A1 | 12/2004 | Wise et al. | |
| 2004/0260164 A1 | 12/2004 | Kilcoyne et al. | |
| 2005/0013685 A1 | 1/2005 | Ricketts et al. | |
| 2005/0015014 A1 | 1/2005 | Fonseca et al. | |
| 2005/0043601 A1 | 2/2005 | Kilcoyne et al. | |
| 2005/0049634 A1 | 3/2005 | Chopra | |
| 2005/0080346 A1 | 4/2005 | Gianchandani et al. | |
| 2005/0090719 A1 | 4/2005 | Scheiner et al. | |
| 2005/0099270 A1* | 5/2005 | Diorio | G06K 19/0723 340/10.51 |
| 2005/0103114 A1 | 5/2005 | Bly et al. | |
| 2005/0154321 A1 | 7/2005 | Wolinsky et al. | |
| 2005/0160825 A1 | 7/2005 | Zdeblick et al. | |
| 2005/0160827 A1 | 7/2005 | Zdeblick et al. | |
| 2005/0187482 A1 | 8/2005 | O'Brien et al. | |
| 2005/0228308 A1 | 10/2005 | Iddan et al. | |
| 2005/0288596 A1 | 12/2005 | Eigler et al. | |
| 2005/0288604 A1 | 12/2005 | Eigler et al. | |
| 2005/0288722 A1 | 12/2005 | Eigler et al. | |
| 2006/0047205 A1 | 3/2006 | Ludomirsky et al. | |
| 2006/0052821 A1 | 3/2006 | Abbott et al. | |
| 2006/0064133 A1 | 3/2006 | Von Arx et al. | |
| 2006/0064134 A1* | 3/2006 | Mazar | A61B 5/0031 607/17 |
| 2006/0064142 A1 | 3/2006 | Chavan et al. | |
| 2006/0064143 A1 | 3/2006 | Von Arx et al. | |
| 2006/0116590 A1 | 6/2006 | Fayram et al. | |
| 2006/0122522 A1 | 6/2006 | Chavan et al. | |
| 2006/0129050 A1 | 6/2006 | Martinson et al. | |
| 2006/0161171 A1 | 7/2006 | Schwartz | |
| 2006/0177956 A1 | 8/2006 | O'Brien et al. | |
| 2006/0178583 A1 | 8/2006 | Montegrande et al. | |
| 2006/0178695 A1 | 8/2006 | Decant, Jr. et al. | |
| 2006/0196277 A1 | 9/2006 | Allen et al. | |
| 2006/0206146 A1 | 9/2006 | Tenerz | |
| 2006/0212047 A1 | 9/2006 | Abbott et al. | |
| 2006/0217762 A1 | 9/2006 | Meahs et al. | |
| 2006/0217763 A1 | 9/2006 | Abbott et al. | |
| 2006/0217764 A1 | 9/2006 | Abbott et al. | |
| 2006/0229488 A1 | 10/2006 | Ayre et al. | |
| 2006/0241354 A1 | 10/2006 | Allen | |
| 2006/0244465 A1 | 11/2006 | Kroh et al. | |
| 2006/0271078 A1 | 11/2006 | Modesitt | |
| 2006/0287602 A1* | 12/2006 | O'Brien | A61B 5/0031 600/486 |
| 2007/0007240 A1 | 1/2007 | Wise et al. | |
| 2007/0028698 A1 | 2/2007 | Guziak et al. | |
| 2007/0032734 A1 | 2/2007 | Najafi et al. | |
| 2007/0049980 A1 | 3/2007 | Zielinski et al. | |
| 2007/0049984 A1 | 3/2007 | Osypka | |
| 2007/0060959 A1 | 3/2007 | Salo et al. | |
| 2007/0073351 A1 | 3/2007 | Zielinski et al. | |
| 2007/0088388 A1 | 4/2007 | Opolski et al. | |
| 2007/0096715 A1 | 5/2007 | Joy et al. | |
| 2007/0100215 A1 | 5/2007 | Powers et al. | |
| 2007/0106246 A1 | 5/2007 | Modesitt | |
| 2007/0106328 A1 | 5/2007 | Wardle et al. | |
| 2007/0106333 A1 | 5/2007 | Fernandez | |
| 2007/0112358 A1 | 5/2007 | Abbott et al. | |
| 2007/0118039 A1 | 5/2007 | Bodecker et al. | |
| 2007/0142727 A1* | 6/2007 | Zhang | A61B 5/0031 600/486 |
| 2007/0149880 A1 | 6/2007 | Willis | |
| 2007/0160748 A1 | 7/2007 | Schugt et al. | |
| 2007/0210786 A1 | 9/2007 | Allen et al. | |
| 2007/0249950 A1* | 10/2007 | Piaget | A61B 5/0031 600/529 |
| 2007/0274565 A1* | 11/2007 | Penner | A61B 5/0031 382/103 |
| 2008/0015421 A1 | 1/2008 | Penner | |
| 2008/0067874 A1* | 3/2008 | Tseng | A61C 17/224 307/104 |
| 2008/0077016 A1* | 3/2008 | Sparks | A61B 5/0031 600/459 |
| 2008/0194925 A1* | 8/2008 | Alsafadi | A61B 5/0002 600/301 |
| 2008/0281212 A1* | 11/2008 | Nunez et al. | 600/508 |
| 2009/0115396 A1 | 5/2009 | Allen et al. | |
| 2009/0189741 A1 | 7/2009 | Rowland et al. | |
| 2009/0224773 A1 | 9/2009 | Joy et al. | |
| 2009/0224837 A1 | 9/2009 | Joy et al. | |
| 2010/0026318 A1 | 2/2010 | Kroh et al. | |
| 2010/0130123 A1* | 5/2010 | Lindman | B63C 11/22 455/3.06 |
| 2010/0161004 A1 | 6/2010 | Najafi et al. | |
| 2010/0308974 A1 | 12/2010 | Rowland et al. | |

OTHER PUBLICATIONS

Collins, Carter, Miniature Passive Pressure Transensor for Implanting in the Eye, Transactions on Bio-Medical Engineering, vol. BME-14, No. 2, pp. 74-83, Apr. 1967.

Nagumo, J., Uchiyama, A., Kimoto, S., Watanuki, T., Hori, M., Suma, K., Ouchi, A., Kumano, M., and Watanabe, H., Echo Capsule for Medical Use (A Batteryless Endoradiosonde), IRE Transaction on Bio-Medical Electronics, pp. 195-199, 1962.

Haynes, H.E. & Witchey, A.L., Medical Electronics: The Pill That "Talks", DEP, 1960, pp. 52-54, Camden, N.J.

The International Bureau of WIPO, International Search Report and Written Opinion of International Searching Authority, Endotronix, Inc., PCT Application No. PCT/US2012/34979, Nov. 2, 2012.

The International Bureau of WIPO, International Search Report and Written Opinion of International Searching Authority, Endotronix, Inc., PCT Application No. PCT/US2009/39730, Jun. 30, 2009.

* cited by examiner

WIRELESS SENSOR READER

CROSS-REFERENCE TO RELATED APPLICATIONS

This application is a continuation of U.S. patent application Ser. No. 13/455,776 entitled "WIRELESS SENSOR READER," filed on Apr. 25, 2012, which claims priority to Provisional Patent Application No. 61/478,647 entitled "WIRELESS SENSOR READER TUNING BASED ON AMBIENT CONDITION," filed on Apr. 25, 2011, and which is a continuation-in-part of U.S. patent application Ser. No. 13/423,693 entitled "WIRELESS SENSOR READER," filed on Mar. 19, 2012, which is a continuation of U.S. patent application Ser. No. 12/419,326 entitled "WIRELESS SENSOR READER," filed on Apr. 7, 2009, which is a continuation-in-part of U.S. patent application Ser. No. 12/075,858 filed on Mar. 14, 2008, which claims priority to U.S. Provisional Application No. 60/918,164 filed on Mar. 15, 2007 each of which are hereby incorporated by reference in their entirety.

FIELD OF INVENTION

The present invention generally relates to an apparatus and device for measuring a wireless signal from a sensor.

BACKGROUND

Wireless sensor and reader systems may be designed to wirelessly monitor the status of a remote sensor. Some such wireless systems include a sensor that transduces a physical parameter into a signal frequency. A reader is then configured to receive and measure the frequency of the sensor signal.

FIG. 1 illustrates an example of an operational frequency bandwidth of a wireless sensor/reader system and the corresponding parameter. As shown, the corresponding parameter is pressure, however it will be appreciated that the concept described herein may apply to any transduced parameter. The exemplary frequency range of the illustrated wireless sensor is from 13 to 14 MHz, which corresponds to absolute pressures of 550-900 mmHg. In the example shown in FIG. 1, frequency is inversely proportional to pressure.

In wireless sensor/reader systems, the sensor may be stimulated by a transmit pulse from a reader, causing the sensor to emit a ring back or "ring" signal at its resonant frequency once that stimulus is removed. The reader may measure the frequency of the ring signal and use a calibration table or formula to determine the sensed pressure.

The ring signal, as received at the reader, may be low power and may decay very quickly, particularly if the distance between sensor and reader is great. This is a problem with all similar wireless sensor systems, whether the systems utilizes a transmit signal that is fixed or swept. Other types of wireless sensor systems, such as those based on grid-dip techniques, may require a relatively long time and many transmit cycles to identify the sensor's resonance frequency, especially when the possible range of resonance frequencies is large.

Some wireless reader/sensor system designs require a gauge pressure reading, meaning pressure relative to local atmospheric pressure. In such designs, however, the sensor is often located at a position where it cannot access atmospheric pressure and thus cannot directly deliver a gauge pressure reading. For example, a blood pressure sensor implanted in the pulmonary artery is not capable of directly accessing atmospheric pressure. To deal with certain medical conditions, clinicians typically wish to know the gauge pressure of the pulmonary artery across a range of 100 mmHg. However, the implanted sensor has no way of knowing what the local atmospheric pressure is. In other words, the implanted sensor is only capable of sensing absolute pressure.

One solution is to place an ambient pressure sensor in the reader. The reader then measures absolute pressure from the implanted sensor, as well as absolute atmospheric ambient pressure from its ambient pressure sensor, and subtracts the ambient pressure from the absolute pressure to obtain gauge pressure.

The example in FIG. 1 illustrates a pressure range between 550-900 mmHg absolute. Ambient pressures in the inhabited regions of earth typically range from 550-800 mmHg absolute. Thus, to measure 0-100 mmHg gage, a sensor's absolute range must go from 550 mmHg (lowest ambient 550 mmHg plus lowest gauge 0 mmHg) to 900 mmHg (highest ambient 850 mmHg plus highest gauge 100 mmHg).

Therefore, there is a need to measure the frequency of a weak signal where the signal's full scale range is wide, but where only a small subset of that full range is used for any individual measurement.

Regardless of the method used to determine the sensor signal frequency, various circuits within the reader must be adapted or tuned to capture the maximum amount of energy in the sensor signal without capturing unwanted energy from sources other than the sensor, such as natural or man-made noise. For example, the reader's receiver antenna and internal filters, such as analog or digital filters, may be tuned to a passband that passes any possible frequency at which the sensor might resonate and rejects all frequencies outside that passband. However, widening the passbands of antennas and filters can cause problems, including higher attenuation, lower signal-to-noise ratios, and increased susceptibility to unwanted interfering signals.

Fixed frequency systems have difficulty overcoming these problems. Some swept frequency systems may attempt to overcome the problems by constantly re-tuning the receivers and filters to match the instantaneous frequency being transmitted. This, however, usually requires significant additional circuitry and processing.

Therefore, an improved method and apparatus are needed.

SUMMARY

A reader device is provided to interface with a wireless sensor. The reader emits a short pulse of energy or a short burst of radio frequency energy to cause the wireless sensor to ring. Immediately after the transmission, the reader receives and amplifies the sensor signal, then sends the signal to a phase-locked loop ("PLL") that locks to the sensor ring frequency. Once the PLL has locked to the ring frequency, the PLL's voltage controlled oscillator ("VCO") is placed in a hold mode to maintain the VCO frequency at the locked frequency. The VCO frequency is counted to determine the sensor resonant frequency.

The reader may include a device, such as a second sensor, to determine a set of possible frequency values of the ring signal. The components of the reader device may be tuned to the set of possible frequency values that are identified.

BRIEF DESCRIPTION OF THE DRAWINGS

Objects and advantages together with the operation of the invention may be better understood by reference to the detailed description taken in connection with the following illustrations, wherein.

DETAILED DESCRIPTION

Figure 1:
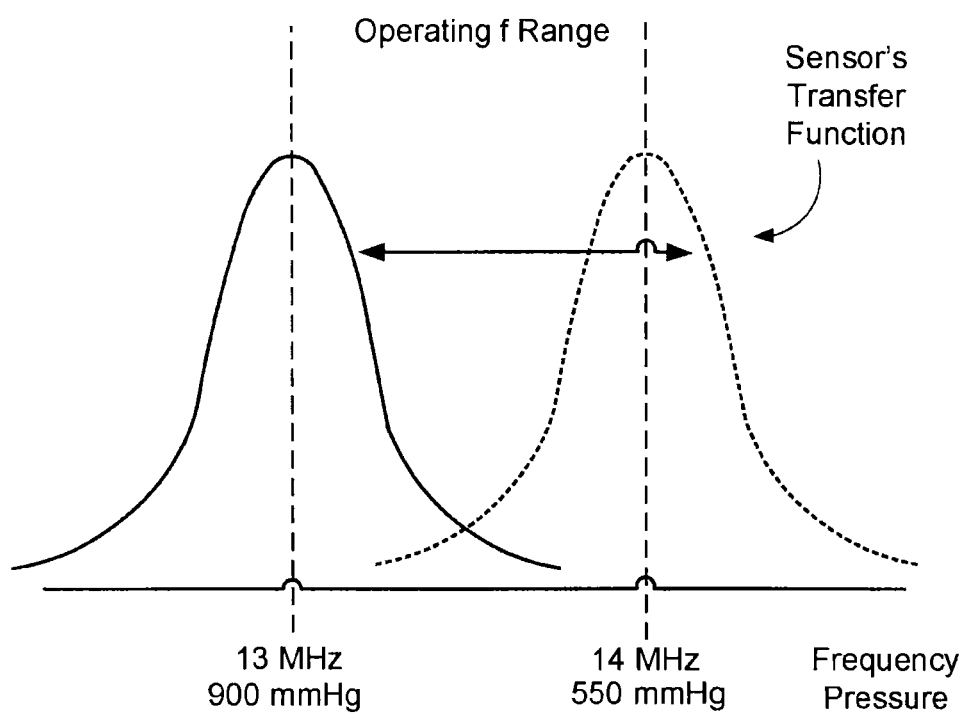
FIG. 1 is a graph of an operational frequency bandwidth of a sensor and corresponding parameter.
Figure 2:
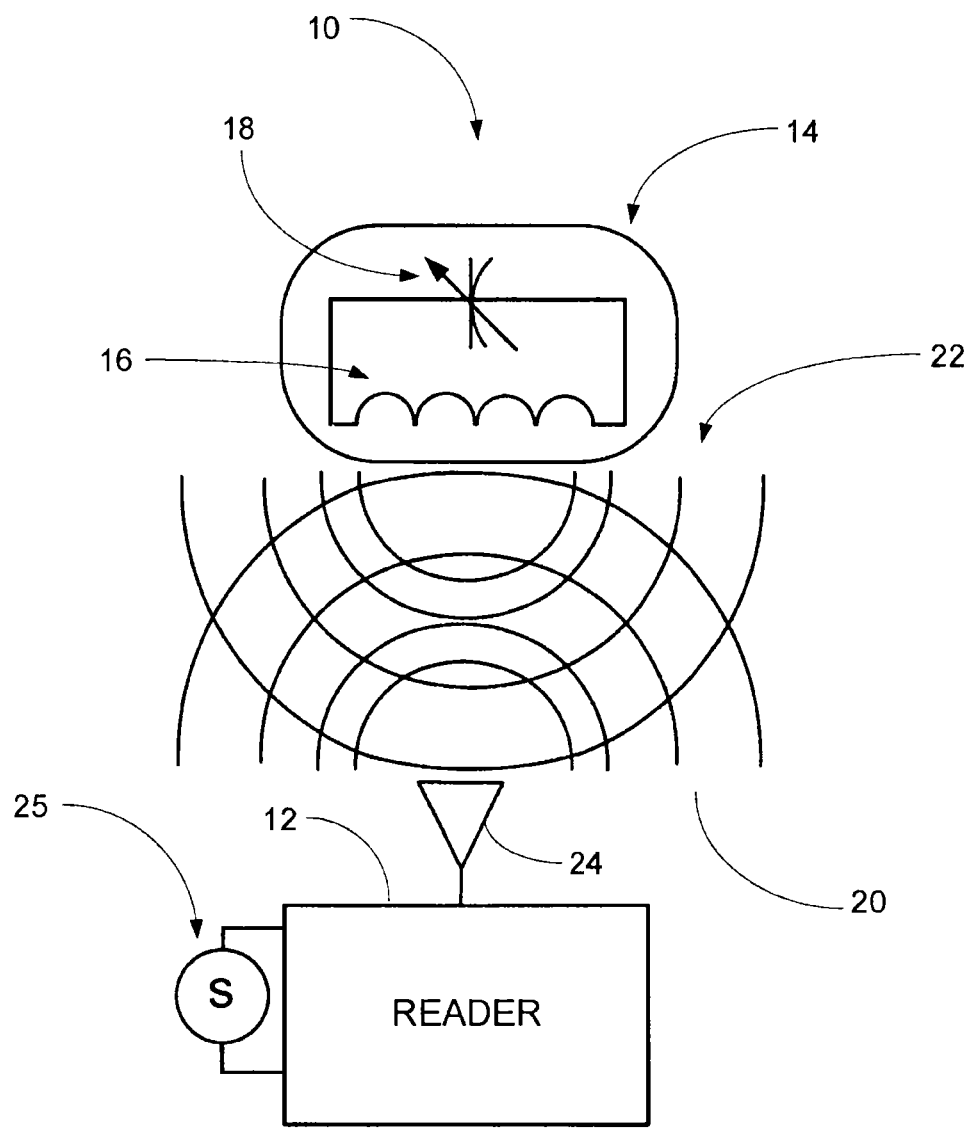
FIG. 2 is an embodiment of a wireless sensor system.

Reference will now be made in detail to exemplary embodiments of the present invention, examples of which are illustrated in the accompanying drawings. It is to be understood that other embodiments may be utilized and structural and functional changes may be made without departing from the respective scope of the present invention.

A wireless system 10 is generally provided. The wireless system 10 may include a wireless reader 12 and a wireless sensor 14. The wireless sensor 14 may be a passive device, such as a device comprising a capacitor 16 and an inductor 18, or an active device. The wireless sensor 14 may be implantable, such as implantable into a living being. For example, the wireless sensor 14 may be implanted in a human body to monitor a condition or parameter within the human body.

The reader 12 may be configured to transmit an excitation pulse 20 to excite the sensor 14. The excitation pulse 20 may cause the sensor 14 to ring or emit a ring signal 22 at its resonant frequency. The resonant frequency of the sensor 14 may vary based on a parameter sensed by the sensor 14. The reader 12 may measure the frequency of the ring signal 22 and determine the sensed parameter. For example, the reader 12 may utilize a formula, lookup table or calibration table to determine the sensed parameter.

The reader 12 may include a receiver to receive the ring signal 22 from the sensor 14. The receiver may comprise an antenna 24 or any other signal receiving device. The receiver may further include one or more filters, such as for example analog or digital filters, to filter the signal 22 received from the sensor 14. The filters may be tuned to a passband to allow a desired frequency bandwidth to be received by the reader 12. The passband may be narrowed to pass only a frequency band that corresponds to a specific parametric range of interest 26, shown in FIG. 3.

Exemplary embodiments described herein may make reference to monitoring and sensing a specific parameter, such as pressure. It will be appreciated, however, that the systems and methods set forth herein may be applied to any measured or sensed parameter, such as pressure, temperature, or any other parameter.

Figure 3:
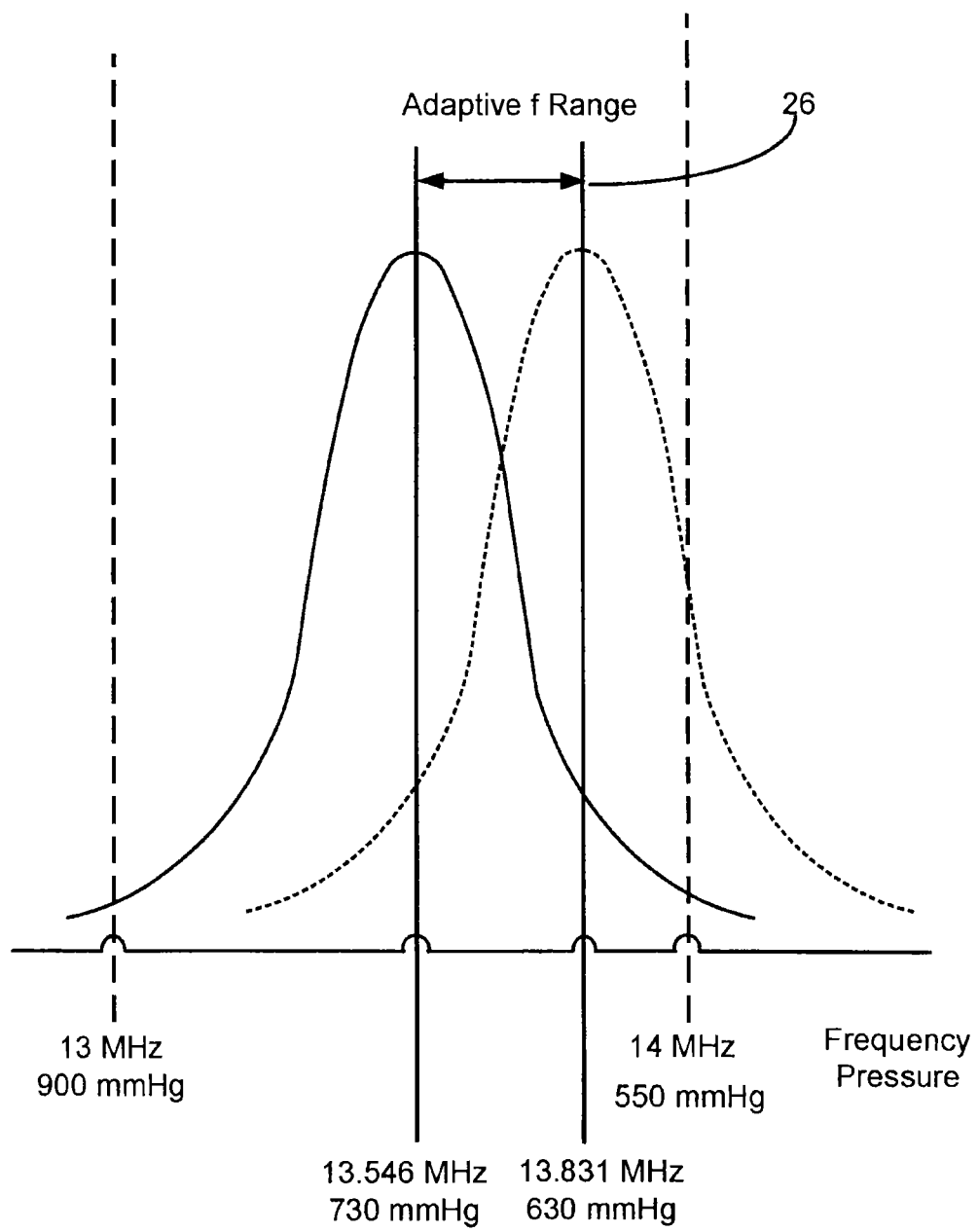
FIG. 3 is a graph of an operational frequency bandwidth of a sensor and corresponding parameter and bandpass window.

By way of a non-limiting example, a wireless system 10 adapted to sense a pressure, such as blood pressure, may include filters to narrow the passband window 26 to only receive frequencies that correspond to pressures within a 100 mmHg gauge pressure range. An example of this passband range 26 is illustrated in FIG. 3. The frequencies that correspond to pressures within a 100 mmHg gauge pressure range may be a "passband window" or "window of interest" 26 of the frequencies that provide the optimal or most valuable data. It will be appreciated, however, that the passband window 26 may correspond to any appropriate range of the sensed parameter.

The spectral location of the passband window 26 within the total range of absolute pressure may vary to capture the desired data. For example, the location of the window 26 may be determined based on the ambient pressure at the time the reader 12 is receiving the ring signal 22 from the sensor 14. To that end, the reader 12 may include an ambient sensor 25, such as an ambient pressure sensor, to sense an ambient condition, such as pressure. The ambient sensor 25 may be embedded in or located on the reader 12. The ambient sensor 25 may also be located away from the reader 12, such as part of another device or system that communicates its ambient reading to the reader 12 or to a third party processor, for determining the location of the passband window 26.

As shown in the graph illustrated in FIG. 3, the passband window 26 may be optimally located based on the ambient pressure measured by the reader's ambient pressure sensor 25. For example, in an embodiment where the sensor is a wireless pressure sensor implanted in the pulmonary artery of a human being, the pressure range of interest is 0-100 mmHg above ambient. Therefore, the Reader's processor would be programmed to locate a passband window 26 such that its edges are at frequencies corresponding to the ambient pressure reading, and a pressure that is 100 mmHg greater than the ambient pressure reading, as shown in FIG. 3. Accordingly, the reader 12 may tune its antenna 24, as well as its internal circuits and algorithms, to focus the passband window 26 near the ambient pressure.

In an embodiment, a wireless sensor 14 may be implanted into a human being located at relatively high altitude, for example an altitude having an ambient pressure near 630 mmHg absolute. The pressure range of interest may therefore be 630-730 mmHg absolute, corresponding to a frequency passband window 26 of 13.831-13.546 MHz. The reader 12 may measure the ambient pressure using its ambient pressure sensor 25. The reader 12 may then determine, from the ambient pressure measurement, the subset of the full-scale frequency range that will contain the remote sensor's frequency. The reader 12 may then tune its receiver, such as the antennas 24, filters, amplifiers, other circuits, or algorithms, to pass the desired subset and block the unwanted portion of the range. For example, the reader 12 may increase the Q of its receiving antenna by narrowing its bandwidth to match the frequency window 26. Additionally, the reader 12 may increase the gain and signal-to-noise ratio of one or more amplifiers in the receive chain by tuning them to the passband window 26. The reader 12 may also tune filters in the receive chain to match the passband window 26, and thus filter out any noise or interference outside the passband window 26. The reader 12 may take numerous pressure readings from the sensor and average them (in its own embedded processor or in a remote processor) to further improve accuracy. The averaging processor may implement an algorithm by which all readings that fall outside the passband window 26 are considered spurious outliers and are not included in the average.

This system and method, as described, provide several advantages over known systems and methods. For example, restricting the passband window 26 of the received ring signal 22 may allow a sensor 14 with a higher Q to be used, thus providing a longer decay time and higher ring signal 22 amplitude. Restricting the passband window 26 also allows for receiver antennas 24 and filters having a higher Q to be used, thus increasing signal to noise ratio. Further, in systems that utilize a fixed-frequency excitation pulse 20, the sensor's transfer function roll-off dictates that the ring signal 22 may be weaker when the sensor 14 is near the edges of its operational frequency range. Adapting the reader's circuitry to focus on bands near the edges may compensate for this effect.

Once the passband window 26 has been determined, many of the reader's internal components may be tuned to focus only on the range of the passband window 26. For example, the reader's receive antenna 24 may be tuned to the passband window 26 containing the ring signal 22. This may be accomplished by switching reactive components in and out of the antenna circuit, including parts of the antenna 24, or by other methods known in the art.

The wireless system 10 may include an amplifier section. The amplifier section may include filters and amplifiers. The filters and amplifiers may be adaptively tuned to the frequency passband window 26 that contains the ring signal 22. This can be accomplished by switching reactive components in and out of the amplifier and filter circuits, or by other methods known in the art.

The wireless system 10 may include at least one phase lock loop (PLL) to lock onto and help determine the ring frequency. The initial reference frequency for the PLL may be set to approximately the center of the frequency passband window 26. This will reduce the time it takes for the PLL to lock onto the ring signal 22 frequency. For example, the reader 12 processor may calculate or look up the control voltage of the PLL's voltage controlled oscillator (VCO) that corresponds to the center of the passband window 26, as defined by the reader's ambient pressure sensor 25. Other methods and circuits for locking and pre-locking the PLL may be used in conjunction with the systems and methods described herein.

The excitation pulse 20 emitted by the reader 12 may be held at an approximately fixed frequency. The fixed excitation pulse 20 may be adapted to be located near the center of the passband window 26 containing the ring signal 22. As a result, the system may utilize a sensor 14 having a higher Q that may provide a stronger, longer lasting ring signal 22.

The wireless system 10 may utilize a swept frequency excitation pulse 20. The bandwidth of the swept frequency excitation pulse 20 may be limited to the passband window 26 containing the ring signal 22. Limiting the excitation pulse 20 in this manner may reduce the time required to acquire the ring signal 22 and allow more samples to be taken for a given pressure instance.

The parameter measured by the sensor 14 may be static or quasi-static in comparison to the speed of measurement. By way of a non-limiting example, a measured blood pressure waveform may be static or quasi-static in comparison to the speed of measurement. In such circumstances, the reader 12 may take multiple readings of the sensor 14 measurement and average them using a processing algorithm. For example, as the ring signal 22 gets weaker and the signal-to-noise ratio (SNR) decreases, the number of noisy, spurious readings may increase. The reader 12 may be configured to ignore any measurements that lie outside the passband window 26 during the averaging process to remove outlying and inaccurate data.

The reader 12 may sample the incoming ring signal 22 and compare the input data with the passband window 26. Based on the comparison, the input data from the ring signal 22 may be stored or discarded. The reader 12 may also optimize or enhance processing of the signal, for example with FFT methods, by only processing portions of the signal that are within the allowed frequency band based on the filtered passband window 26. Other methods of improving the measurement of the received signal based on narrowing the allowed frequency band to match the ambient measurement may also be utilized.

The examples used herein are directed to an ambient pressure reading to determine a narrowed bandwidth for the absolute reading and adapt the reader 12 circuitry and/or algorithms to that bandwidth. It will be appreciated, however, that this method may be used in any circumstance where two sensor measurements are taken and the result of one measurement can be used to limit the possible outcomes of the other measurement. The sensed parameter is not limited to pressure but may be any parameter. Further, the wireless sensors 14 and ambient sensor do not necessarily have to measure the same quantity or parameter but may instead measure different quantities or parameters.

Although the embodiments of the present invention have been illustrated in the accompanying drawings and described in the foregoing detailed description, it is to be understood that the present invention is not to be limited to just the embodiments disclosed, but that the invention described herein is capable of numerous rearrangements, modifications and substitutions without departing from the scope of the claims hereafter. The claims as follows are intended to include all modifications and alterations insofar as they come within the scope of the claims or the equivalent thereof.

We claim:

1. A method of obtaining a measurement from a remote location, the method comprising:
    transmitting a plurality of excitation pulses each at a predetermined frequency to a wireless sensor;
    receiving a signal from said wireless sensor at a reader in response to said plurality of excitation pulses;
    sampling and holding said received signal;
    ascertaining the frequency of said received signal;
    wherein said wireless sensor is configured to change its resonant frequency in proportion to at least one sensed parameter; and
    wherein said reader is configured to define a band of resonant frequency values, to optimize itself for operation based on said band wherein said reader is in communication with an ambient pressure sensor configured to at least partially define the band of resonant frequency values.

2. The method of claim 1 further comprising generating a count signal at a frequency to match the frequency of said signal from said wireless sensor.

3. The method of claim 2, wherein said count signal is generated by a voltage controlled oscillator.

4. The method of claim 2, wherein the frequency of said count signal is an integer multiple of said received signal frequency.

5. The method of claim 1, wherein said wireless sensor is a passive sensor.

6. The method of claim 5, wherein said wireless sensor comprises at least one inductor and at least one capacitor.

7. The method of claim 6, wherein at least one of said at least one inductor and said at least one capacitor changes its value in response to said at least one sensed parameter.

8. The method of claim 1, wherein each of said excitation pulses is a different frequency.

9. The method of claim 1, wherein said signal from said wireless sensor is a ring signal.

10. The system of claim 1, wherein the predetermined frequency is at least partially determined based on readings from said ambient pressure sensor.

11. A system for obtaining a measurement from a remote location, said system comprising:
    a wireless sensor configured to change its resonant frequency in proportion to at least one sensed parameter;
    a reader configured to transmit an excitation pulse at only a fixed frequency to said wireless sensor and to receive a signal from said wireless sensor in response to said excitation pulse, the reader includes an ambient pressure sensor; and wherein said reader is configured to define a band of resonant frequency values, to optimize itself for operation based on said band, wherein said reader is in communication with the ambient pressure sensor configured to at least partially define the band of resonant frequency values.

12. A system for obtaining a measurement from a remote location, the system comprising:
a wireless sensor is configured to change its resonant frequency in proportion to at least one sensed parameter;
a reader configured to transmit a plurality of excitation pulses at a fixed frequency to said wireless sensor and to receive at least one signal from said wireless sensor in response to said excitation pulses;
wherein said reader is configured to define a band of resonant frequency values, to optimize itself for operation based in said band wherein said reader is in communication with an ambient pressure sensor wherein said reader is configured to at least partially define the band of resonant frequency values.

13. The system of claim 12, wherein said plurality of excitation pulses are spaced apart at time intervals.

14. The system of claim 12, wherein said reader includes a circuitry configured to generate a count signal at a frequency to match the frequency of said signal from said wireless sensor.

15. The system of claim 14, wherein said count signal is generated by a voltage controlled oscillator.

16. The system of claim 14, wherein the frequency of said count signal is an integer multiple of said frequency of said signal from said wireless sensor.

17. The system of claim 12, wherein said wireless sensor is a passive sensor.

18. The system of claim 17, wherein said wireless sensor comprises at least one inductor and at least one capacitor.

19. The system of claim 18, wherein at least one of said at least one inductor and said at least one capacitor changes its value in response to said at least one sensed parameter.

20. The system of claim 12, wherein said signal from said wireless sensor is a ring signal.

21. The system of claim 12, wherein each of said excitation pulses is transmitted at a predetermined frequency.

22. A method of obtaining a measurement from a remote location, the method comprising:
transmitting a plurality of excitation pulses from a reader each at a predetermined frequency to a wireless sensor wherein the predetermined frequency is at least partially determined by an ambient pressure sensor;
receiving a signal from said wireless sensor in response to said plurality of excitation pulses;
sampling and holding said received signal;
ascertaining the frequency of said received signal;
wherein said wireless sensor is configured to change its resonant frequency in proportion to at least one sensed parameter; and
wherein said reader is in communication with said ambient pressure sensor and is configured to at least partially define a band of resonant frequency values, to optimize itself for operation based in said band.

23. The method of claim 22 further comprising generating a count signal at a frequency to match the frequency of said signal from said wireless sensor.

24. The method of claim 23, wherein said count signal is generated by a voltage controlled oscillator.

25. The method of claim 23, wherein the frequency of said count signal is an integer multiple of said received signal frequency.

26. The method of claim 22, wherein said wireless sensor is a passive sensor.

27. The method of claim 26, wherein said wireless sensor comprises at least one inductor and at least one capacitor.

28. The method of claim 27, wherein at least one of said at least one inductor and said at least one capacitor changes its value in response to said at least one sensed parameter.

29. The method of claim 22, wherein each of said excitation pulses is a different frequency.

30. The method of claim 22, wherein said signal from said wireless sensor is a ring signal.

31. A system for obtaining a measurement from a remote location, the system comprising:
a wireless reader configured to transmit a plurality of excitation pulses to a wireless sensor and receive a signal from said wireless sensor in response to said plurality of excitation pulses, wherein said wireless reader is configured to sample and hold said received signal to ascertain the frequency of said received signal;
wherein said wireless sensor is configured to change its resonant frequency in proportion to at least one sensed parameter; and
wherein said reader is in communication with an ambient pressure sensor wherein said reader is configured to at least partially define a band of resonant frequency values, to optimize itself for operation based in said band.

32. The system of claim 31, wherein said plurality of excitation pulses are spaced apart at time intervals.

33. The system of claim 31, wherein said wireless reader includes a circuitry configured to generate a count signal at a frequency to match the frequency of said signal from said wireless sensor.

34. The system of claim 33, wherein said count signal is generated by a voltage controlled oscillator.

35. The system of claim 33, wherein the frequency of said count signal is an integer multiple of said frequency of said signal from said wireless sensor.

36. The system of claim 31, wherein said wireless sensor is a passive sensor.

37. The system of claim 36, wherein said wireless sensor comprises at least one inductor and at least one capacitor.

38. The system of claim 37, wherein at least one of said at least one inductor and said at least one capacitor changes its value in response to said at least one sensed parameter.

39. The system of claim 31, wherein each of said excitation pulses is a different frequency.

40. The system of claim 31, wherein said signal from said wireless sensor is a ring signal.

41. The system of claim 31, wherein each of said excitation pulses is transmitted at a predetermined frequency.

* * * * *